(12) United States Patent
Struelens et al.

(10) Patent No.: US 8,716,543 B2
(45) Date of Patent: May 6, 2014

(54) PROCESS TO MAKE PROPYLENE FROM ETHYLENE AND EITHER DIMETHYL ETHER, OR METHANOL AND DIMETHYL ETHER

(75) Inventors: Pieter Struelens, Gooik (BE); Pierre Jacobs, Gooik (BE); Nikolai Nesterenko, Nivelles (BE); Delphine Minoux, Nivelles (BE); Sander Van Donk, Guildford (GB); Jean-Pierre Dath, Beloeil (BE)

(73) Assignee: Total Research & Technology Feluy, Seneffe (Feluy) (BE)

( * ) Notice: Subject to any disclaimer, the term of this patent is extended or adjusted under 35 U.S.C. 154(b) by 0 days.

(21) Appl. No.: 13/581,817

(22) PCT Filed: Mar. 15, 2011

(86) PCT No.: PCT/EP2011/053906
§ 371 (c)(1),
(2), (4) Date: Oct. 15, 2012

(87) PCT Pub. No.: WO2011/113837
PCT Pub. Date: Sep. 22, 2011

(65) Prior Publication Data
US 2013/0137914 A1     May 30, 2013

(30) Foreign Application Priority Data
Mar. 16, 2010 (EP) .................................... 10156630

(51) Int. Cl.
*C07C 1/20*     (2006.01)

(52) U.S. Cl.
USPC ............................ 585/639; 585/638; 585/640

(58) Field of Classification Search
USPC ............................................... 585/638–640
See application file for complete search history.

(56) References Cited

U.S. PATENT DOCUMENTS

| | | | |
|---|---|---|---|
| 3,906,054 A | 9/1975 | Kaeding et al. | |
| 3,911,041 A | 10/1975 | Kaeding et al. | |
| 5,573,990 A | 11/1996 | Wang et al. | |
| 6,797,851 B2 | 9/2004 | Martens et al. | |
| 2004/0122267 A1* | 6/2004 | Sher et al. | 585/324 |
| 2006/0020155 A1* | 1/2006 | Beech et al. | 585/639 |
| 2006/0229482 A1* | 10/2006 | Setoyama et al. | 585/638 |
| 2009/0326298 A1* | 12/2009 | Bozzano | 585/639 |
| 2010/0256431 A1 | 10/2010 | Nesterenko et al. | |
| 2011/0124939 A1 | 5/2011 | Minoux et al. | |

FOREIGN PATENT DOCUMENTS

WO     2009055997 A1     5/2009

OTHER PUBLICATIONS

Eckehart et al. Zeolites. Ullmann's Encyclopedia of Industrial Chemistry. 2000. pp.p.9.*

Jinzhe Li, et al.; "Co-Reaction of Ethene and Methylation Agents Over SAPO-34 and ZSM-22"; Catalysis Letters, vol. 121, No. 3-4, pp. 303-310; 2008; CODEN: CALEER; ISSN: 1011-372X; XP002589055.

Qingjun Zhu, et al.; "Activation of Hydrocarbons on Acidic Zeolites: Superior Selectivity of Methylation of Ethene With Methanol to Propene on Weakly Acidic Catalysts"; Chemical Communications (Cambridge, United Kingdom), vol. 41; pp. 5164-5166; 2008; CODEN: CHCOFS; ISSN: 1359-7345; XP002589056.

* cited by examiner

*Primary Examiner* — Walter D Griffin
*Assistant Examiner* — Jelitza Perez

(57) ABSTRACT

A process to make propylene can include providing a reaction zone containing a catalyst and introducing a feedstock into the reaction zone. The catalyst can be an acid. The feedstock can include ethylene, dimethyl ether or methanol and dimethyl ether with at least 1000 wppm of dimethyl ether, and optionally steam. The feedstock can be contacted with the catalyst at temperature and pressure conditions to produce an effluent, including propylene, hydrocarbons, steam, optionally unconverted methanol and/or unconverted dimethyl ether and optionally unconverted ethylene. The temperature at the inlet of the reaction zone can be under 280° C., such as from 50 to 280° C. The effluent can be sent to a fractionation zone to recover propylene, optionally methanol, dimethyl ether and optionally ethylene. At least a part of methanol, dimethyl ether, and ethylene can be recycled to the reaction zone at step b).

18 Claims, No Drawings

PROCESS TO MAKE PROPYLENE FROM ETHYLENE AND EITHER DIMETHYL ETHER, OR METHANOL AND DIMETHYL ETHER

CROSS-REFERENCE TO RELATED APPLICATIONS

This application claims the benefit of PCT/EP2011/053906, filed Mar. 15, 2011, which claims priority from EP 10156630.5, filed Mar. 16, 2010.

FIELD OF THE INVENTION

The present invention relates to a process to make propylene from ethylene and methanol or dimethyl ether.

Olefins are traditionally produced from petroleum feedstocks by catalytic or steam cracking processes. These cracking processes, especially steam cracking, produce light olefin(s), such as ethylene and/or propylene, from a variety of hydrocarbon feedstock. Ethylene and propylene are important commodity petrochemicals useful in a variety of processes for making plastics and other chemical compounds. The limited supply and increasing cost of crude oil has prompted the search for alternative processes for producing hydrocarbon products. The MTO process produces light olefins such as ethylene and propylene as well as heavy hydrocarbons such as butenes. Said MTO process is the conversion of methanol or dimethylether by contact with a molecular sieve. The interest in the methanol to olefin (MTO) process is based on the fact that methanol can be obtained from coal or natural gas by the production of synthesis gas which is then processed to produce methanol. Olefins can also be produced by dehydration of the corresponding alcohol. Ethanol can be obtained by fermentation of carbohydrates. Made up of organic matter from living organisms, biomass is the world's leading renewable energy source.

Driven by the consumption of the derivatives such as polypropylene, the demand for propylene is recently growing faster than that of ethylene, leading to an increased interest in developing propylene production technologies. The present invention relates to this technology.

BACKGROUND OF THE INVENTION

WO 2009055997 describes a process for producing propylene from ethylene and methanol (or/and dimethyl ether), which is characterized in that the gas containing methanol (or/and dimethyl ether) and the gas containing ethylene are contacted together with a catalyst which has a pore diameter of 0.3 nm-0.5 nm and a saturated NH3 adsorption amount of 0.8 mmol/g-2.5 mmol/g at 200° C., to obtain the products containing propylene. The reaction conditions are as follows: the molar ratio of ethylene/methanol (or 2 times dimethyl ether) is 0.1-2, the reaction temperature is 300-600° C., preferably 350° C.-550° C. and the reaction pressure is 0.01-0.8 MPa. The propylene yield of products may be more than 60 C % based on the methanol. In the examples the catalyst is a SAPO 34 and the reaction temperature is 400° C. This reaction is not selective, it produces also C3-C6.

In "Co-reaction of ethene and methanol over modified H-ZSM-5" by Jinzhe Li et al published in Catalysis Communications 9 (2008) pages 2515-2519 is described the co reaction of ethylene and methanol over HZSM-5, P-La modified ZSM-5 (PLaHZ) and hydrothermal-treated PLaHZ catalysts. The reaction temperatures are from 450° C. to 550° C. At 500° C., methanol WHSV=3.5 h-1, ethene WHSV=5.7 h-1, time on stream (TOS)=6 min, the methanol conversion is 60.8%, the ethylene conversion is 11.3%, the production comprises 52.9% of propylene, 19.8% of butenes and 24% of C5+. With the same operating conditions at TOS=100 minutes the propylene % increases to about 70%.

In "Direct observation of olefin homologations on zeolite ZSM-22 and its implications to methanol to olefin conversion" by Zhi-Min Cui et al published in Journal of Catalysis 258 (2008) pages 83-86 is described olefin homologation (methylation of the olefin C=C double bond) on ZSM-22. Homologation of ethylene, propylene and styrene were directly observed between $^{13}C$ labeled methanol and olefins. Isotopic tracking shows high selectivity for homologation reaction, e.g. from ethylene, propene has one $^{13}C$ atom, butene has two $^{13}C$ atoms, and pentene has three $^{13}C$ atoms. The reaction temperatures are from 300° C. to 400° C., the production comprises about similar proportions of propylene, butene and pentene.

U.S. 2006-0229482 describes a process for producing propylene, comprising: contacting a reaction mixture of ethylene and methanol and/or dimethyl ether in the presence of a catalyst while controlling the amount of ethylene that is discharged from the reaction system to a reduced level in comparison to the amount of ethylene that is being fed into the reaction system, and while controlling the yield of propylene to at least 40 mol %, based on the sum of the number of moles of methanol and two times the number of moles of dimethyl ether, which are being fed into the reaction system. The reaction temperature employed depends on the type of the catalyst used, but is usually at least about 200° C., preferably at least about 250° C., more preferably at least about 300° C., and the upper limit is usually at most about 700° C., preferably at most about 600° C., more preferably at most about 500° C. The reaction Conditions are:

Reaction temperature: 400° C.
Methanol: 6.5 mol %
Ethylene/methanol (molar ratio)=5
Water/methanol (molar ratio)=4
Methanol WHSV=0.5 $h^{-1}$ The methanol conversion is 100%, the catalyst is ZSM-5 or SAPO-34 and the hydrocarbon composition in the discharged component from the reactor comprises 61 to 73% of ethylene, 14 to 28% of propylene and 3 to 10% of butene. All examples are made with CH3OH at 400° C. or above.

WO 2007 135053 describes a process for the preparation of C5 and/or C6 olefins from a lower olefin, which lower olefin comprises from 2 to 5 carbon atoms, and an oxygenate, which oxygenate comprises at least one oxygen-bonded alkyl group, comprising contacting the lower olefin with the oxygenate, in a molar ratio of oxygen-bonded alkyl group to lower olefin of at least 1:1 in the presence of a MTT-type zeolite. In example 1 and comparative example A 2-methyl-2-butene (2M2B) and dimethylether (DME) were reacted in a molar feed ratio 2M2B:DME of 2:1 over a MFI-type (comparative) and a MTT-type zeolite (according to the invention) at a temperature of 325° C. In example 2,2-methyl-2-butene (2M2B) and dimethylether (DME) were reacted in a molar feed ratio 2M2B:DME of 2:1 over a MTT-type zeolite at a temperature of 450° C.

It has now been discovered that propylene can be efficiently produced from DME or DME+MeOH and ethylene at temperature below 300° C. with selectivity higher than 60% on the base on converted carbon. Without being binded by any explanation it seems that the introduction of an ethylene containing feedstock in the DME feed changes the usual MTO reaction route to more kinetically quick homologation. Moreover, under these conditions the contribution of oligomerization/cracking reactions is relatively low and may be even more suppressed in the presence of steam at the inlet of reactor. This leads to very high propylene selectivity from ethylene and MeOH (the precursor of DME). The propylene selectivity on carbon basis is the wt ratio of carbon in propylene in the reactor effluent (outlet of the reactor) to the converted carbon in the reactor. The proposed solution allows producing propylene with a selectivity higher than 60% on carbon basis.

BRIEF SUMMARY OF THE INVENTION

The present invention is a process to make propylene comprising:
a) providing a reaction zone containing a catalyst;
b) introducing a feedstock comprising ethylene, dimethyl ether or a mixture of methanol and dimethyl ether comprising at least 1000 wppm of dimethyl ether, optionally steam into said reaction zone and into contact with said catalyst;
c) operating said reaction zone at temperature and pressure conditions to produce an effluent comprising propylene, hydrocarbons, steam, optionally unconverted methanol and/or unconverted dimethyl ether and optionally unconverted ethylene;
d) sending the effluent of step c) to a fractionation zone to recover propylene optionally methanol and for dimethyl ether and optionally ethylene;
e) optionally recycling at least a part of methanol and/or dimethyl ether and optionally recycling at least a part of ethylene to the reaction zone at step b);
wherein the catalyst is an acid and the temperature at the inlet of the reaction zone is under 280° C. and advantageously from 50 to 280° C.

In a preferred embodiment the temperature at the inlet of the reaction zone ranges from 150° C. to 260° C.

The "inlet of the reaction zone" means the part of the reaction zone at which ethylene, dimethyl ether or methanol and dimethyl ether are introduced into said reaction zone.

In an embodiment, ethylene and optionally steam can be introduced in the reaction zone as a feedstock 1 and dimethyl ether or methanol and dimethyl ether and optionally steam as a feedstock 2. In an embodiment feedstock 1 or feedstock 2 or both feedstock 1 and feedstock 2 can be divided in a plurality of streams. In these embodiments the "temperature at the inlet of the reaction zone" as mentioned above is the temperature of the catalyst at each introduction of a new feedstock.

In an embodiment the catalyst can be an heteropoly acid or a supported heteropoly acid. Said heteropolyacids are soluble in water or polar oxygenated hydrocarbons, such as alcohols or ethers.

In another embodiment (preferred) the catalyst is solid.

DETAILED DESCRIPTION OF THE INVENTION

As regards the operating conditions, the pressure can be from 0.001 to 10 MPa. The WHSV of the sum of (i) ethylene and of (ii) dimethyl ether or methanol and dimethyl ether can be from 0.01 to 100 h$^{-1}$.

Optionally the ethylene containing feedstock is subjected to a contact with the catalyst in presence of steam. Water concentration can be such as, at the inlet of the reactor, the mole ratio of water to the sum of the number of moles of methanol and two times the number of moles dimethyl ether is from at least 0.005 to at most 20.

Optionally the ethylene feedstock diluted with some inert medium is provided for the reaction zone. The possible examples of the inert medium could be the gases such as nitrogen, CO2, CO, H2, N2, Methane, He, Argon etc.

DME is much more active in homologation of ethylene than methanol. Therefore in a preferred embodiment the MeOH is converted at least partially to DME rich feedstock before co-reacting with ethylene. Such conversion can be performed in a separate dehydration zone and then sent to the reaction zone a). Optionally water can be removed in whole or in part between the dehydration zone and the reaction zone a).

In an embodiment the feedstock of step b) comprises at least 2000 wppm of dimethyl ether.

By way of example DME comprising up to 10 w % MeOH are convenient feedstocks.

The ethylene containing feedstock can be mixed with MeOH/DME feed before the reaction zone a) or fed as two separate streams in the reaction zone a). The MeOH/DME containing feed can by introduced in the reaction zone a) by one injection point or could be added by quenching across the reaction zone a).

It should be noted that the amount of MeOH and DME could be added by quenching or by a separate stream. The overall mole ratio C2=/(MeOH+2DME) can be from 0.05 to 20.

With respect to the feedstock composition, in a preferred case the molar amount of ethylene being fed to the reaction system as a blended stream with methanol and or DME is higher than 0.2 relative to the molar amount of carbon being fed to the reaction system in form of methanol and dimethyl ether, i.e. the amount of ethylene being fed to the reaction zone a) is usually at least 0.2, preferably at least 0.3, more preferably at least 0.45, as determined by the mole ratio of ethylene to the sum of the number of moles of methanol and two times the number of moles of dimethyl ether. On the other hand, if the amount of ethylene is too greatly in excess, problems arise which include costs, the amount of by-products formed and cumbersomeness of operations, and the like. Accordingly, as the upper limit, the amount of ethylene being fed to the reaction system is usually at most 10, more preferably at most 9, particularly preferably at most 8, as a molar ratio, to the sum of the number of moles of methanol and two times the number of moles of dimethyl ether.

The reaction mode in the process of the present invention is not particularly limited and a known gas phase reaction process using a fluidized bed, a moving bed, slurry reactor, catalytic distillation reactor or a fixed bed reactor, is employed. Further, the reaction may be carried out as a batch system, a semicontinuous system or a continuous system, but it is preferred to carry it out as a continuous system. Such a method may be a method employing a single reactor or a method employing a plurality of reactors disposed in series or in parallel.

Optionally the feedstock is subjected to a contact with the catalyst under such conditions when at least one of the feedstock components is in a liquid phase.

As regards the catalyst of the reaction zone a), it could be any, provided it is an acid.
the catalyst can be P-ZSM-5,
the catalyst can be P-ZSM-5 prepared according to specific procedure given in WO2009016156 and WO/2009/098262, the content of which are incorporated in the present application;
The catalyst can be a phosphorous modified zeolite;
the catalysts can be phosphated zeolites or crystalline metalaluminophosphates containing 8 or 10 member rings;
the catalyst can be heteropoly acid or supported heteropoly acid the catalyst can be crystalline molecular sieve selected from the group of MFI, MEL, FER, MTT, MWW, TON, EUO, MFS, ZSM-48, CHA, ERI, AEI, LEV, the catalyst can be an acid catalyst containing mesopores or both micro- and mesopores;

the catalyst can be based on alumina or silica-alumina with different porosity;

said catalyst can contain specific metals selected from the group of Li, Na, Mg, Ca, Sr, Y, La, Ni, Cu, Ce, Zn, Ag, Ga, Co, Mo, W, Re or a mixture thereof For example, a known catalyst may be used such as a solid acid catalyst of e.g. a clay mineral such as kaolin or leached kaolin. Another type of catalyst is that of a carrier such as clay which supports an acid such as sulfuric acid or phosphoric acid. Still other types are an acid type ion exchange resin; an aluminum phosphate; a mesoporous silica alumina such as Al-MCM41 or Al-MCM48; a zeolite; or a lamellar zeolite such as ITQ-2.

For example, a known catalyst may be used such as a solid acid catalyst of e.g. a zeolite, the structure of the zeolite may, for example, be those identified in terms of the codes of the International Zeolite Association (IZA), which are AEI, AET, AEL, AFI, AFO, AFS, AST, ATN, BEA, CAN, CHA, DDR, EMT, ERI, EUO, FAU, FER, LEV, LTL, MAZ, MEL, MFI, MOR, MTT, MTW, MWW, OFF, PAU, RHO, STT, TON, and the like.

Preferred among these zeolites are those that have micropores having a pore diameter ranging from 3 to 6 Å and including at least one 8 or 10 members ring into the structure.

It is by way of example of the MFI (ZSM-5, silicalite-1, boralite C, TS-1), MEL (ZSM-11, silicalite-2, boralite D, TS-2, SSZ-46), FER (Ferrierite, FU-9, ZSM-35), MTT (ZSM-23), MWW (MCM-22, PSH-3, ITQ-1, MCM-49), TON (ZSM-22, Theta-1, NU-10), EUO (ZSM-50, EU-1), MFS (ZSM-57), ZSM-48, CHA, ERI, AEI, LEV family of microporous materials consisting of silicon, aluminium, boron and oxygen.

The dealuminated crystalline silicate is advantageously such as about 10% by weight of the aluminium is removed. Such dealumination can be done by any conventional techniques known per se but is advantageously made by a steaming optionally followed by a leaching.

In a specific embodiment the crystalline silicate is steamed to remove aluminium from the crystalline silicate framework. The steam treatment is conducted at elevated temperature, preferably in the range of from 425 to 870° C., more preferably in the range of from 540 to 815° C. and at atmospheric pressure and at a water partial pressure of from 13 to 200 kPa. Preferably, the steam treatment is conducted in an atmosphere comprising from 5 to 100% steam. The steam atmosphere preferably contains from 5 to 100 vol % steam with from 0 to 95 vol % of an inert gas, preferably nitrogen. A more preferred atmosphere comprises 72 vol % steam and 28 vol % nitrogen i.e. 72 kPa steam at a pressure of one atmosphere. The steam treatment is preferably carried out for a period of from 1 to 200 hours, more preferably from 20 hours to 100 hours. As stated above, the steam treatment tends to reduce the amount of tetrahedral aluminium in the crystalline silicate framework, by forming alumina.

In a specific embodiment the external surface of molecular sieves is passivitated.

In a specific embodiment the molecular sieve is subjected to alumination in order to increase the acidity of the catalyst.

In a specific embodiment the proton acid sites are partially exchanged with metal cations selected from the group of Li, Na, Mg, Ca, Sr, Y, La, Ni, Cu, Ce, Zn, Ag, Ga, Co, Mo, W, Re or a mixture of thereof.

In a specific embodiment the catalyst is an heteropoly acid or supported heteropoly acid. Heteropoly acids form by condensation of two or more oxyacids, e. g., phosphoric or silicic acid with tungstic acid, and contain large polyoxometallate anions with interstitial hydrated protons and variable levels of water of hydration.

The heteropolyacid anion comprises from two to eighteen oxygen-linked polyvalent metal atoms, which are generally known as the "peripheral" atoms. These peripheral atoms surround one or more central atoms in a symmetrical manner. The peripheral atoms are usually one or more of molybdenum, tungsten, vanadium, niobium, tantalum and other metals. The central atoms are usually silicon or phosphorus but can comprise any one of a large variety of atoms from Groups I-VIII in the Periodic Table of elements. These include, for instance, cupric ions; divalent beryllium, zinc, cobalt or nickel ions; trivalent boron, alulllinium, gallium, iron, cerium, arsenic, antimony, phosphorus, bismuth, chromium or rhodium ions; tetravalent silicon, germianium, tin, titanium, zirconium, vanadium, sulphur, tellurium, manganese nickel, platinum, thorium, hafnium, cerium ions and other rare earth ions; pentavalent phosphorus, arsenic, vanadium, antimony ions; hexavalent tellurium ions; and heptavalent iodine ions. Such heteropolyacids are also known as "polyoxoanions", "polyoxometallates" or "metal oxide clusters".

The heteropolyacids are soluble in water or polar oxygenated hydrocarbons, such as alcohols or ethers. The particular heteropoly acids of the present catalysts are acids with anions adopting the well known Keggin or Wells-Dawson or Anderson-Evans-Perloff primary structures and are represented by formulas: $H_3[PW12O_{40}]xH_2O$ (phosphotungstic acid or 12-tungstophosphoric acid), and $H_4[SiW_{12}O_{40}]xH_2O$ (12-tungstosilicic acid or silicotungstic acid). They contain a central tetrahedral $PO_4$ or $SiO_4$ group connected to 12 surrounding $WO_3$ octahedra and can be considered the condensation product of phosphoric or silicic acid with tungstic acid.

These water soluble acids can be deposited on supports by impregnation techniques well known to those skilled in the art such as by an incipient wetness technique.

In another specific embodiment the crystalline silicate catalyst is mixed with a binder, preferably an inorganic binder, and shaped to a desired shape, e.g. pellets.

As regards the phosphorus modified zeolites as a catalyst, they can be prepared based on MFI, MOR, MEL, clinoptilolite or FER crystalline aluminosilicate molecular sieves having an initial Si/Al ratio advantageously between 4 and 500. The P-modified zeolites of this recipe can be obtained based on cheap crystalline silicates with low Si/Al ratio (below 30).

By way of example said P-modified zeolite is made by a process comprising in that order:

selecting a zeolite (advantageously with Si/Al ratio between 4 and 500) among $H^+$ or $NH_4^+$-form of MFI, MEL, FER, MOR, clinoptilolite;

introducing P at conditions effective to introduce advantageously at least 0.05 wt % of P;

separation of the solid from the liquid if any;

an optional washing step or an optional drying step or an optional drying step followed by a washing step;

a calcination step; The zeolite with low Si/Al ratio has been made previously with or without direct addition of an organic template.

Optionally the process to make said P-modified zeolite comprises the steps of steaming and leaching. The method consists in steaming followed by leaching. It is generally known by the persons in the art that steam treatment of zeolites, results in aluminium that leaves the zeolite framework and resides as aluminiumoxides in and outside the pores of the zeolite. This transformation is known as dealumination of zeolites and this term will be used throughout the text. The treatment of the steamed zeolite with an acid solution results in dissolution of the extra-framework aluminiumoxides. This transformation is known as leaching and this term will be used throughout the text. Then the zeolite is separated, advantageously by filtration, and optionally washed. A drying step can be envisaged between filtering and washing steps. The solution after the washing can be either separated, by way of example, by filtering from the solid or evaporated.

P can be introduced by any means or, by way of example, according to the recipe described in U.S. Pat. No. 3,911,041, U.S. Pat. No. 5,573,990 and U.S. Pat. No. 6,797,851.

The catalyst made of a P-modified zeolite can be the P-modified zeolite itself or it can be the P-modified zeolite formulated into a catalyst by combining with other materials that provide additional hardness or catalytic activity to the finished catalyst product.

The separation of the liquid from the solid is advantageously made by filtering at a temperature between 0-90° C., centrifugation at a temperature between 0-90° C., evaporation or equivalent.

Optionally, the zeolite can be dried after separation before washing. Advantageously said drying is made at a temperature between 40-600° C., advantageously for 1-10 h. This drying can be processed either in a static condition or in a gas flow. Air, nitrogen or any inert gases can be used.

The washing step can be performed either during the filtering (separation step) with a portion of cold (<40° C.) or hot water (>40 but <90° C.) or the solid can be subjected to a water solution (1 kg of solid/4 liters water solution) and treated under reflux conditions for 0.5-10 h followed by evaporation or filtering.

Final calcination step is performed advantageously at the temperature 400-700° C. either in a static condition or in a gas flow. Air, nitrogen or any inert gases can be used.

According to a specific embodiment the phosphorous modified zeolite is made by a process comprising in that order:
- selecting a zeolite (advantageously with Si/Al ratio between 4 and 500, from 4 to 30 in a specific embodiment) among $H^+$ or $NH_4^+$-form of MFI, MEL, FER, MOR, clinoptilolite;
- steaming at a temperature ranging from 400 to 870° C. for 0.01-200 h;
- leaching with an aqueous acid solution at conditions effective to remove a substantial part of Al from the zeolite;
- introducing P with an aqueous solution containing the source of P at conditions effective to introduce advantageously at least 0.05 wt % of P;
- separation of the solid from the liquid;
- an optional washing step or an optional drying step or an optional drying step followed by a washing step;
- a calcination step.

Optionally between the steaming step and the leaching step there is an intermediate step such as, by way of example, contact with silica powder and drying.

In an embodiment the leaching is made with with an aqueous acid solution containing the source of P at conditions effective to remove a substantial part of Al from the zeolite and to introduce P. This can replace the step of introduction of P.

Advantageously the selected MFI, MEL, FER, MOR, clinoptilolite (or $H^+$ or $NH_4^+$-form MFI, MEL, FER, MOR, clinoptilolite) has an initial atomic ratio Si/Al of 100 or lower and from 4 to 30 in a specific embodiment. The conversion to the $H^+$ or $NH_4^+$-form is known per se and is described in U.S. Pat. No. 3,911,041 and U.S. Pat. No. 5,573,990.

Advantageously the final P-content is at least 0.05 wt % and preferably between 0.3 and 7 w %. Advantageously at least 10% of Al, in respect to parent zeolite MFI, MEL, FER, MOR and clinoptilolite, have been extracted and removed from the zeolite by the leaching.

Then the zeolite either is separated from the washing solution or is dried without separation from the washing solution. Said separation is advantageously made by filtration. Then the zeolite is calcined, by way of example, at 400° C. for 2-10 hours.

In the steam treatment step, the temperature is preferably from 420 to 870° C., more preferably from 480 to 760° C. The pressure is preferably atmospheric pressure and the water partial pressure may range from 13 to 100 kPa. The steam atmosphere preferably contains from 5 to 100 vol % steam with from 0 to 95 vol % of an inert gas, preferably nitrogen. The steam treatment is preferably carried out for a period of from 0.01 to 200 hours, advantageously from 0.05 to 200 hours, more preferably from 0.05 to 50 hours. The steam treatment tends to reduce the amount of tetrahedral aluminium in the crystalline silicate framework by forming alumina.

The leaching can be made with an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The other inorganic acids may comprise an inorganic acid such as nitric acid, hydrochloric acid, methansulfuric acid, phosphoric acid, phosphonic acid, sulfuric acid or a salt of such an acid (e.g. the sodium or ammonium salts) or a mixture of two or more of such acids or salts.

The residual P-content is adjusted by P-concentration in the aqueous acid solution containing the source of P, drying conditions and a washing procedure if any. A drying step can be envisaged between filtering and washing steps.

Said P-modified zeolite can be used as itself as a catalyst. In another embodiment it can be formulated into a catalyst by combining with other materials that provide additional hardness or catalytic activity to the finished catalyst product. Materials which can be blended with the P-modified zeolite can be various inert or catalytically active materials, or various binder materials. These materials include compositions such as kaolin and other clays, various forms of rare earth metals, phosphates, alumina or alumina sol, titania, zirconia, quartz, silica or silica sol, and mixtures thereof. These components are effective in densifying the catalyst and increasing the strength of the formulated catalyst. The catalyst may be formulated into pellets, spheres, extruded into other shapes, or formed into a spray-dried particles. The amount of P-modified zeolite which is contained in the final catalyst product ranges from 10 to 90 weight percent of the total catalyst, preferably 20 to 70 weight percent of the total catalyst.

The formation of propene by methylation of ethene with methanol/DME could be useful in adjusting propene to ethene ratio in MTO process, in improving the propylene/ethylene ratio from the steam crackers as well as in transformation of dilute ethene into propylene in FCC dry gas. The advantage of this reaction lies in a very high selectivity to propylene limiting the formation of by-products. In particular cases ethylene can partially be transformed to propylene in DME reactor using a specific catalyst optionally integrated with MTO plant.

EXAMPLES

Example 1

Samples of zeolite MFI with atomic ratio Si/Al=11.5 (CBV2314), Si/Al=140 (CBV28014), Si/Al=550 (CP7123), a sample of zeolite MTT with atomic ratio Si/Al=24 (Z02K019E), a sample of zeolite FER with atomic ratio Si/Al=33 (CP914) with a crystal size <1 µm in $NH_4$-form has been obtained from Zeolyst Int®. The sample is hereinafter identified as A, B, C, D, and E respectively. Before use as catalysts the samples were calcined in air at 550° C. for 6 h.

Example 2

Catalyst test was performed on 1 g (grain size: 250-500 µm) of catalyst A with a feed containing He—35 ml/min, ethylene—0.42 g/h, DME—0.62 g/h, MeOH—0.04 g/h, H2O—0.03 g/h at inlet reaction temperature 235° C. in a fixed-bed, down flow reactor at atmospheric pressure. Prior to catalytic run the catalyst was heated in flowing $N_2$ flow at 400° C. for 4 h followed by cooling down to the reaction temperature. Analysis of the products has been performed on-line by a gas chromatograph equipped with a capillary column. The catalyst test was carried out for 15 hours-on-stream. The average selectivity to propylene at steady state was 76.1% at conversion of DME—1.2%, and at conversion of ethylene—1.6%. The results are given on carbon free dry basis, coke free basis.

Example 3

Catalyst test was performed on 1 g (grain size: 250-500 µm) of catalyst B with a feed containing He—35 ml/min, ethylene—0.42 g/h, DME—0.62 g/h, MeOH—0.04 g/h, H2O—0.03 g/h at inlet reaction temperature 235° C. in a fixed-bed, down flow reactor at atmospheric pressure. Prior to catalytic run the catalyst was heated in flowing $N_2$ flow at 400° C. for 4 h followed by cooling down to the reaction temperature. Analysis of the products has been performed on-line by a gas chromatograph equipped with a capillary column. The catalyst test was carried out for 6 hours-on-stream. The average selectivity to propylene at steady state was 75.3% at conversion of DME—2%, and at conversion of ethylene—2%. The results are given on carbon free dry basis, coke free basis.

Example 4

Catalyst test was performed on 1 g (grain size: 250-500 µm) of catalyst C with a feed containing He—35 ml/min, ethylene—0.42 g/h, DME—0.62 g/h, MeOH—0.04 g/h, H2O—0.03 g/h at inlet reaction temperature 250° C. in a fixed-bed, down flow reactor at atmospheric pressure. Prior to catalytic run the catalyst was heated in flowing $N_2$ flow at 400° C. for 4 h followed by cooling down to the reaction temperature. Analysis of the products has been performed on-line by a gas chromatograph equipped with a capillary column. The catalyst test was carried out for 15 hours-on-stream. The average selectivity to propylene at steady state was 100% at conversion of DME—2.5%, and at conversion of ethylene—1%. The results are given on carbon free dry basis, coke free basis.

Example 5

Catalyst test was performed on 1 g (grain size: 250-500 µm) of catalyst D with a feed containing He—35 ml/min, ethylene—0.42 g/h, DME—0.62 g/h, MeOH—0.04 g/h, H2O—0.03 g/h at inlet reaction temperature 250° C. in a fixed-bed, down flow reactor at atmospheric pressure. Prior to catalytic run the catalyst was heated in flowing $N_2$ flow at 400° C. for 4 h followed by cooling down to the reaction temperature. Analysis of the products has been performed on-line by a gas chromatograph equipped with a capillary column. The catalyst test was carried out for 15 hours-on-stream. The average selectivity to propylene at steady state was 69% at conversion of DME—5%, and at conversion of ethylene—5.6%. The results are given on carbon free dry basis, coke free basis.

Example 6

Catalyst test was performed on 1 g (grain size: 250-500 µm) of catalyst A with a feed containing He—35 ml/min, ethylene—0.42 g/h, DME—0.62 g/h at inlet reaction temperature 225° C. in a fixed-bed, down flow reactor at atmospheric pressure. Prior to catalytic run the catalyst was heated in flowing $N_2$ flow at 400° C. for 4 h followed by cooling down to the reaction temperature. Analysis of the products has been performed on-line by a gas chromatograph equipped with a capillary column. The catalyst test was carried out for 15 hours-on-stream. The average selectivity to propylene at steady state was 80.8% at conversion of DME—14.4%, and at conversion of ethylene—5.0%. The results are given on carbon free dry basis, coke free basis.

Example 7

Catalyst test were performed on 1 g (grain size: 250-500 µm) of catalyst D with a feed containing He—35 ml/min, ethylene—0.42 g/h, DME—0.62 g/h at inlet reaction temperature 250° C. in a fixed-bed, down flow reactor at atmospheric pressure. Prior to catalytic run the catalyst was heated in flowing $N_2$ flow at 400° C. for 4 h followed by cooling down to the reaction temperature. Analysis of the products has been performed on-line by a gas chromatograph equipped with a capillary column. The catalyst test was carried out for 15 hours-on-stream. The average selectivity to propylene at steady state was 65.7% at conversion of DME—6.8%, and at conversion of ethylene—6.5%. The results are given on carbon free dry basis, coke free basis.

Example 8

Catalyst test were performed on 1 g (grain size: 250-500 µm) of catalyst E with a feed containing $N_2$—22 ml/min, ethylene—0.345 g/h, DME—0.57 g/h at inlet reaction temperature 160° C. in a fixed-bed, down flow reactor at atmospheric pressure. Prior to catalytic run the catalyst was activated in flowing $N_2$ flow at 400° C. for 4 h followed by cooling down to the reaction temperature. Analysis of the products has been performed on-line by a gas chromatograph equipped with a capillary column. The catalyst test was carried out for 15 hours-on-stream. The selectivity to propylene at steady state was 100 at conversion of DME—3.1%, and at conversion of ethylene—2.4%. The results are given on carbon free dry basis, coke free basis.

Example 9

A commercial sample of SAPO-34 ($1Al_2O_3$:$0.6SiO_2$:$0.94P_2O_5$) with a crystal size about 0.5 µm containing about 980 µmol/g of acid sites (TPD NH$_3$) was used. Before testing in the reaction the sample was calcined in air flow at 600° C. for 10 h.

Catalyst test was performed on 1 g (grain size: 250-500 µm) of the catalyst with a feed containing N$_2$—22 ml/min, ethylene—0.345 g/h, DME—0.57 g/h at inlet reaction temperatures 250° C. in a fixed-bed, down flow reactor at atmospheric pressure. Prior to catalytic run the catalyst was activated in flowing N$_2$ flow at 400° C. for 4 h followed by cooling down to the reaction temperature. Analysis of the products has been performed on-line by a gas chromatograph equipped with a capillary column. The selectivity to propylene at 30 min on stream was 100% at conversion of DME—3.7%, and at conversion of ethylene—1.61%. The results are given on carbon free dry basis, coke free basis.

Example 3-1

Comparative

Catalyst test was performed on 1 g (grain size: 250-500 µm) of catalyst B with a feed containing nitrogen—20 ml/min, ethylene—0.345 g/h, MeOH—0.6 g/h at inlet reaction temperature 250° C. in a fixed-bed, down flow reactor at atmospheric pressure. Prior to catalytic run the catalyst was heated in N$_2$ flow at 400° C. for 4 h followed by cooling down to the reaction temperature. Analysis of the products has been performed on-line by a gas chromatograph equipped with a capillary column. The catalyst test was carried out for 6 hours-on-stream. No propylene was found in the effluent.

This example illustrates that MeOH is much less active than DME in homologation of ethylene and the high selectivity to propylene can be achieved only if the DME is present in the feed.

Example 10

A commercial sample of SAPO-11 provided by Zeolyst Int (ZD09004) containing about 490 µmol/g of acid sites (TPD NH$_3$) was used. Before testing in the reaction, the sample was calcined in air flow at 600° C. for 10 h.

Catalyst test was performed on 1 g (grain size 250-500 µm) of the catalyst with a feed containing N$_2$—22 ml/min, ethylene—0.345 g/h, DME—0.57 g/h at inlet reaction temperatures 250° C. in a fixed-bed, down flow reactor at atmospheric pressure. Prior to catalytic run the catalyst was activated in flowing N$_2$ flow at 400° C. for 4 h followed by cooling down to the reaction temperature. Analysis of the products has been performed on-line by a gas chromatograph equipped with a capillary column. The selectivity to propylene at 120 min on stream was 85% at conversion of DME—3.5%, and at conversion of ethylene—2.8%. The results are given on carbon free dry basis, coke free basis.

The invention claimed is:
1. A process to make propylene comprising:
a) providing a reaction zone containing a catalyst;
b) introducing a feedstock comprising ethylene, dimethyl ether or a mixture of dimethyl ether and up to 10 wt. % of methanol, and optionally steam into said reaction zone and into contact with said catalyst;
c) operating said reaction zone at temperature and pressure conditions to produce an effluent comprising propylene, hydrocarbons, steam, optionally unconverted methanol and/or unconverted dimethyl ether and optionally unconverted ethylene;
d) sending the effluent of step c) to a fractionation zone to recover propylene optionally methanol and/or dimethyl ether and optionally ethylene;
e) optionally recycling at least a part of methanol and/or dimethyl ether and optionally recycling at least a part of ethylene to the reaction zone at step b);
wherein the catalyst is an acid and the temperature at the inlet of the reaction zone is up to 160° C.

2. The process according to claim 1 wherein the WHSV of the sum of (i) ethylene and of (ii) dimethyl ether or methanol and dimethyl ether is from 0.01 to 100 h-1.

3. The process according to claim 1 wherein MeOH is converted at least partially to DME rich feedstock in a separate dehydration zone and then sent to the reaction zone at step a).

4. The process according to claim 1 wherein the amount of ethylene being fed to the reaction zone at step a) is from 0.05 to 20, as determined by the mole ratio of ethylene to the sum of the number of moles of methanol and two times the number of moles of dimethyl ether.

5. The process according to claim 4 wherein the mole ratio of ethylene to the sum of the number of moles of methanol and two times the number of moles of dimethyl ether is at least 0.2.

6. The process according to claim 5 wherein the mole ratio of ethylene to the sum of the number of moles of methanol and two times the number of moles of dimethyl ether is at least 0.3.

7. The process according to claim 6 wherein the mole ratio of ethylene to the sum of the number of moles of methanol and two times the number of moles of dimethyl ether is at least 0.45.

8. The process according to claim 7 wherein the mole ratio of ethylene to the sum of the number of moles of methanol and two times the number of moles of dimethyl ether is under 10.

9. The process according to claim 8 wherein the mole ratio of ethylene to the sum of the number of moles of methanol and two times the number of moles of dimethyl ether is under 9.

10. The process according to claim 9 wherein the mole ratio of ethylene to the sum of the number of moles of methanol and two times the number of moles of dimethyl ether is under 8.

11. The process according to claim 10 wherein the catalyst is a solid catalyst.

12. The process according to claim 11 wherein the catalyst is P-ZSM-5.

13. The process according to claim 11 wherein the catalyst comprises phosphated zeolites or crystalline metalaluminophosphates containing 8 or 10 member rings.

14. The process according to claim 11 wherein the catalyst comprises a crystalline molecular sieve selected from the group MFI, MEL, FER, MTT, MWW, TON, EUO, MFS, ZSM-48, CHA, ERI, AEI, LEV.

15. The process according to claim 14 wherein the catalyst contains Li, Na, Mg, Ca, Sr, Y, La, Ni, Cu, Ce, Zn, Ag, Ga, Co, Mo, W, Re or a mixture thereof.

16. The process according to claim 15 wherein the feedstock of step b) comprises at least 2000 wppm of dimethyl ether.

17. The process according to claim 1, wherein the feedstock is subjected to contact with the catalyst under conditions wherein at least one component of the feedstock is in liquid phase.

18. The process according to claim 11 wherein the catalyst comprises phosphated zeolite.

* * * * *